US006611325B1

(12) United States Patent
Clark

(10) Patent No.: US 6,611,325 B1
(45) Date of Patent: Aug. 26, 2003

(54) ENHANCED DEFECT DETECTION USING SURFACE SCANNING INSPECTION TOOLS

(75) Inventor: Douglas A. Clark, Vancouver, WA (US)

(73) Assignee: Seh-America, Inc., Vancouver, WA (US)

( * ) Notice: Subject to any disclaimer, the term of this patent is extended or adjusted under 35 U.S.C. 154(b) by 0 days.

(21) Appl. No.: 09/525,461

(22) Filed: Mar. 15, 2000

(51) Int. Cl.[7] .............................................. G01N 21/88
(52) U.S. Cl. .................... 356/237.2; 356/237.4
(58) Field of Search ......................... 356/237.2, 237.4, 356/237.8; 382/145; 250/559.45

(56) References Cited

U.S. PATENT DOCUMENTS

| 4,740,708 A | | 4/1988 | Batchelder |
| 4,898,471 A | * | 2/1990 | Vaught et al. ............ 356/237.4 |
| 5,355,212 A | | 10/1994 | Wells et al. |
| 5,535,005 A | * | 7/1996 | Mukherjee-Roy et al. .. 356/600 |
| 5,870,187 A | * | 2/1999 | Uritsky et al. ........... 356/237.2 |
| 5,917,332 A | | 6/1999 | Chen et al. |
| 5,995,217 A | | 11/1999 | Watanabe |
| 5,995,218 A | * | 11/1999 | Ide ........................... 356/237.1 |
| 6,407,809 B1 | * | 6/2002 | Finarov et al. ........... 356/237.3 |

* cited by examiner

Primary Examiner—Zandra V. Smith
(74) Attorney, Agent, or Firm—Oliff & Berridge, PLC

(57) ABSTRACT

A surface scanning inspection system that uses a laser to scan the surface of a wafer for defects. The wafers are pre-aligned at a specified angle prior to the scan. This enables maximum light scattered off stacking fault defects, to be directed into a collector, enhancing the abilities of the system to classify the defect from other type of defects.

27 Claims, 3 Drawing Sheets

SIDE VIEW 510  TOP VIEW 520  ANGLED VIEW 530

ENHANCED DEFECT DETECTION USING SURFACE SCANNING INSPECTION TOOLS

FIELD OF INVENTION

This invention is directed towards the detection of stacking faults found on wafers by using a laser inspection system.

DESCRIPTION OF RELATED ART

During wafer manufacturing and processing, defects can be deposited on the wafers which in turn may cause the device, that is to be fabricated on the wafer, to malfunction. In order to find these defects, several laser inspection tools have been developed. These tools have the ability to scan bare silicon wafers and measure the amount of scattered light, relative to the background level, coming from the laser hitting the wafer. The scattered light is then processed and it is determined whether or not the laser has hit a defect or not. This processing can tell the size and location of a particular defect.

Many of these laser inspection tools and systems do not accurately detect the various defects that occur on silicon wafers and during the manufacturing process. As the feature size of manufactured products decrease, every defect becomes important as even the tiniest defect can cause failures in the device being manufactured on the wafer. Therefore, it becomes increasingly necessary to obtain an accurate and precise detection of these defects.

SUMMARY OF THE INVENTION

Accordingly, the present invention provides systems and methods for improving the detection of defects found on wafers and particularly mound defects found on bare silicon wafers. Since defects can be various shapes, sizes and chemically different, the light scattering off the defect can vary depending upon the different defects on the wafer. Because many defects of similar type are oriented in the same direction on the wafer, the angle at which the wafer is scanned can maximize the light scatter that is collected by the collection optics of the surface scanning inspection system (SSIS).

In a preferred embodiment of the present invention it is necessary to obtain a high accurate count of stacking fault defects that are found on bare silicon wafers. An example of one type of stacking fault defect is mound defects. Mound defects are defined as light point defects (LPD) reported by the Tencor SS6200 laser particle measurement device, that are greater than 20.2 $\mu$m in diameter, latex sphere equivalent (LSE). When the wafers are pre-aligned so that the wafer is rotated 45 degrees from the notch on the wafer and relative to the laser scan path, it is possible to get close to 100 percent, if not a 100 percent, capture rate for all stacking fault defects located on the silicon wafer. Therefore, the amount of defects located on each wafer is known. Thus, improved measurement capability of both the location and density of stacking fault defects provides a more accurate measurement of wafer quality.

BRIEF DESCRIPTION OF THE DRAWINGS

Various exemplary embodiments of this invention will be described in detail, with reference to the following figures, wherein.

DETAILED DESCRIPTION OF PREFERRED EMBODIMENTS

Figure 1:
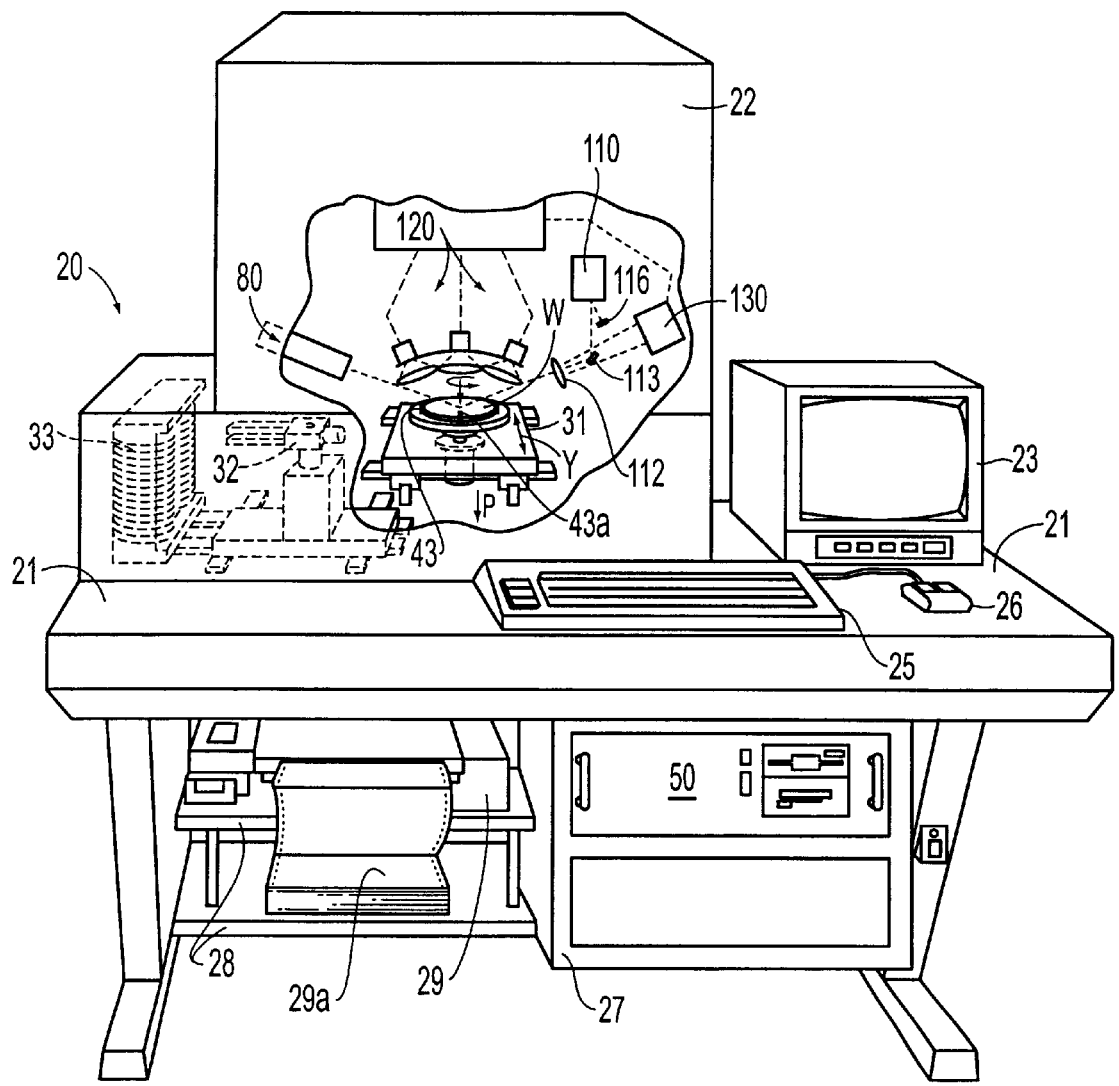
FIG. 1 illustrates an exemplary embodiment of a surface scanning inspection system.

FIG. 1 shows an exemplary embodiment a surface scanning inspection system 20. The surface inspection system detects any flaw on the surface of a silicon wafer 130 that causes an increase of light-scattering. The surface inspection system is preferably used for inspecting the surface of unpatterned wafers 130. However, the surface inspection system may be used to detect defects on patterned wafers 130. The surface inspection system 20 includes means for transporting a wafer 130 along a material path P. The transporting means has the ability to pre-align the wafers outside the scan chamber and may have the ability to rotate the wafer 130 as it travels along the material path P. The surface S of the wafer 130 is then scanned and the scattered and reflected light from the surface S is collected.

The surface inspection system 20, as shown in FIG. 1, is arranged as a workstation. Located at the workstation is a worktable 21, housing 22, video display 23, keyboard 25, and a mouse 26. A cabinet 27, located below the worktable 21, contains a system controller 50. A shelf 28, located adjacent to the cabinet 27, supports a printer 29 and associated printer paper 29a. A robotic wafer handling device 32 is located adjacent the inspection station 20 and is used to load and unload wafers 130 from a cassette 33 onto the table 31. The cassette 33 can hold numerous wafers 130 and is loaded into the cabinet 27 through a door, not shown. The handling of the wafers 130 is done automatically to avoid human contact, thereby reducing the risk of contamination.

The light source 80 is positioned to be able to scan the surface S of the wafer 130 as the wafer travels along the material path P. The wafer 130 can be scanned as it is moving through the system or at a stationary position. The light reflected and scattered off the wafer 130 is then collected by a plurality of dark channel collectors 120 and a light channel detector 110. The light channel collector 110 measures light reflected from the surface of the wafer 130, while the dark channel collector 120 measures scattered light. The light channel detector 110 may be any one of a photodiode, PMT or a quadrant-cell device. The quadrant-cell device is arranged for X-Y coordinate positioning detecting, so that the deviation in the path of reflected and scattered light may be determined. From this collected scattered and reflected light, defect location and size, on the wafer, can be determined.

Figure 2:
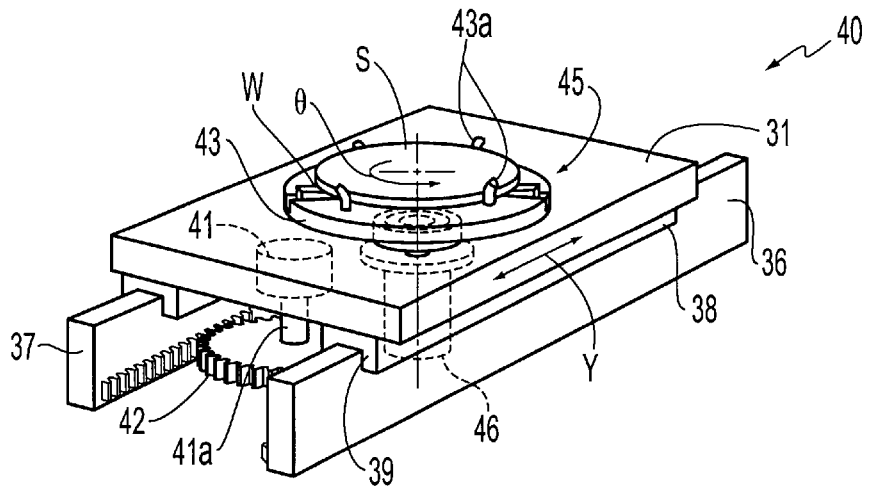
FIG. 2 illustrates an exemplary embodiment of a wafer transferring device of the surface scanning inspection system of FIG. 1.

FIG. 2 shows an exemplary transporting means for the wafer 130 as shown in FIG. 1. The surface scanning inspection system 20 includes the transporting means to transport the wafer 130 along the material path P. The means for transporting the wafer 130 is illustrated as a transporter 40. The transporter 40 includes a gear 42, motor 41, a shaft 41a arranged for rotating the gear 42, and guides 36, 37 having teeth used to guide the transporter 40. The motor 41 and gear 42 mounted on the motor shaft 41a, form a chuck for the system 50. The motor 41 of the chuck is mounted to a stage member 43 having a plurality of flanges 43a extending upwardly therefrom which receives the wafer 130.

The transporter 40 may be capable of rotating the wafer 130. A rotator 45 may be arranged to rotate the wafer 130. The rotator 45 may rotate the wafer 130 to a specified angle or rotate to various angles so that the scanning operations can scan at these angles. It should be noted that various other rotating devices may be used to rotate the wafers 130. In the preferred embodiment the wafers are pre-aligned to the specified angle before placing the wafers 130 in the surface scanning inspection system. It should also be noted that the system 50, that controls the processing of the wafers 130 through the scanning system, may be programmed to scan the wafers 130 at a specified angle.

Figure 3:
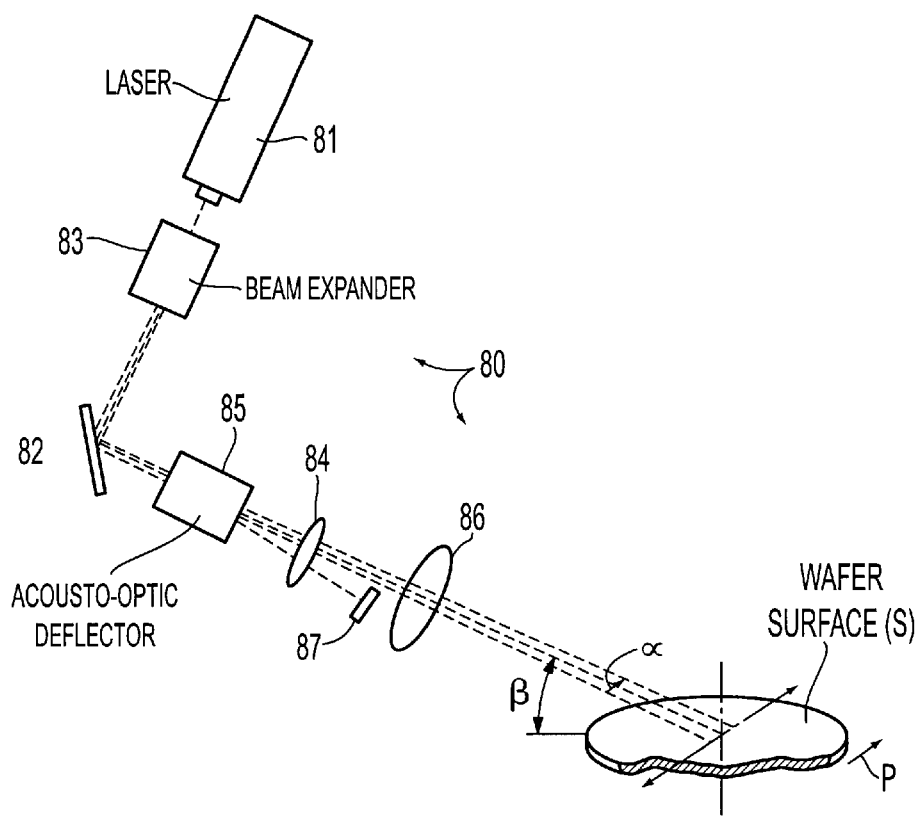
FIG. 3 illustrates an exemplary embodiment of a light source used in the surface scanning inspection system.

FIG. 3 shows an exemplary light source used in the surface scanning inspection system of FIG. 1. The light source 80 includes a laser 81, mirror 82, beam expander 83, lenses 84, 86, deflector 85, and stop member 87. The laser 81 generates a beam of light that is used to scan the surface S of the wafer 130. The associated optics included in the light source 80, generate a linear polarized light. The beam expander 83 is positioned between the laser 81 and the deflector 85 to expand the light beam prior to entering the deflector 85. The beam expander 83 or other devices, such as a polygon mirror, function to scan the beam across the wafer. The deflector 85 is used to deflect the beam of light along a narrow scan path. The deflector can be any number of deflectors, such as a rotating mirror, piezoelectric scanner, or the like.

Figure 4:
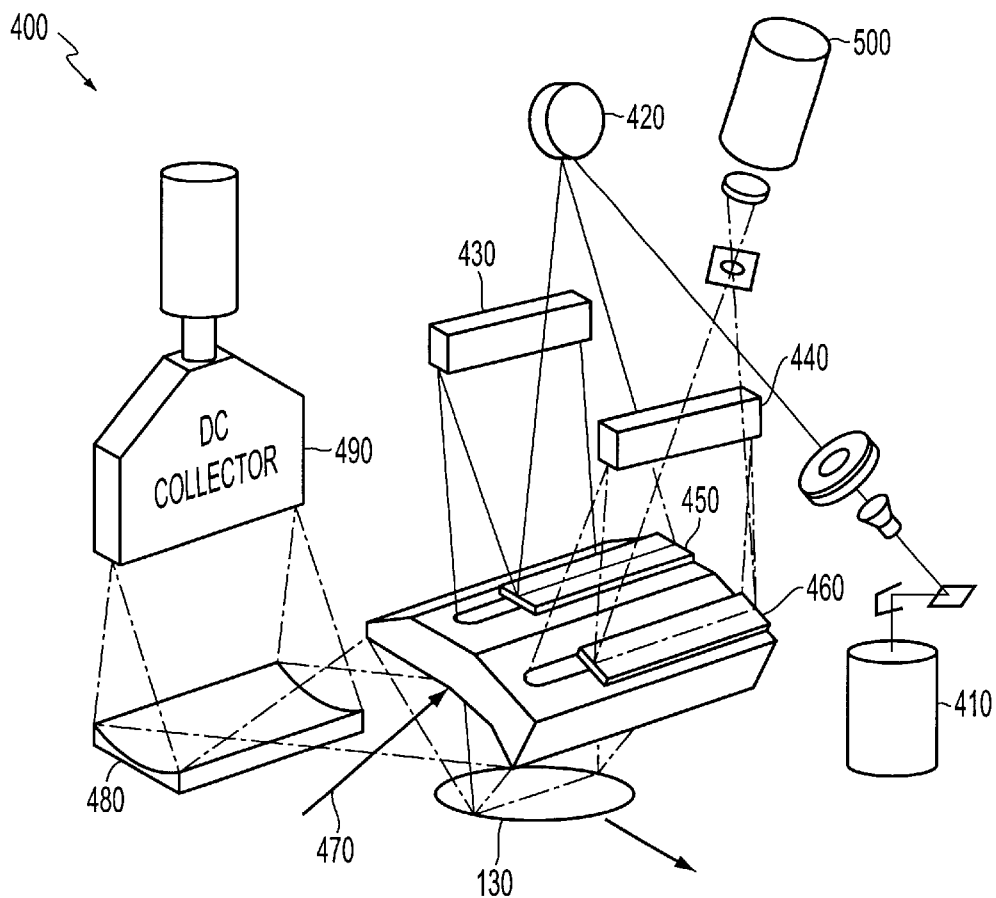
FIG. 4 illustrate a preferred embodiment of a surface scanning inspection system.

FIG. 4 shows an example of a preferred surface scanning inspection system of the present invention. Surface scanning inspection systems of this type can be found in such systems as the CR82e manufactured by ADE Optical Systems, or the like. A light source 410 contains a laser preferably an Argon-Ion laser with the capability of outputting 55 mW. The laser beam is then reflected off mirrors towards a deflector 420. The deflector in this example is polygon mirror capable of dual speed control in order to increase the signal to noise ratio. The light beam is then reflected off reflectors 450 and 430 and directed onto the wafer 130. The light beam scans the wafer and the reflected and scattered light coming off the wafer 130 is directed towards dark and light channel collectors through a series of mirrors. Both reflected 30 and scattered light are collected. The collected light is then digitized and analyzed by the system processor (not shown) of the surface scanning inspection system.

The wafer 130 is scanned in order to detect defects, particles, flaws and the like. However, the detection of the defects and the like depends upon if the scattered light coming off the defect is deflected towards the collection optics. There are many conditions that affect the way that the light is scattered and whether or not it is received by the collection optics. The composition of the defect, shape, texture, size and orientation are some of the characteristics may affect the scattering of the light. Larger defects contain more surface area and thus scatter more light than smaller defects. Defects made up of reflective material scatter more light than defects made up of duller light absorbing material. A rough defect, or one with many facets, reflects light more than defects that have less facets or have rounded edges. The orientation of the defect relative to the collection optics will affect the fraction of light scatter that scatters towards the collection optics, thus affecting the apparent size of that defect.

In order to accurately detect the defects that are located on wafer 130, it is necessary to position, or pre-align the wafer 130 so that the light scattered into the collection optics is maximized. The angle of rotation can depend upon the different defects that are being scanned. The different types of crystallographic defects, can have a maximum light scatter at a different orientation, or rotated angle, of the wafer 130. Therefore, if it is known what the majority of defects are deposited on the wafer, then the wafer 130 can be rotated at a specified angle for that defect, thus accurately detecting all the defects.

Figure 5:
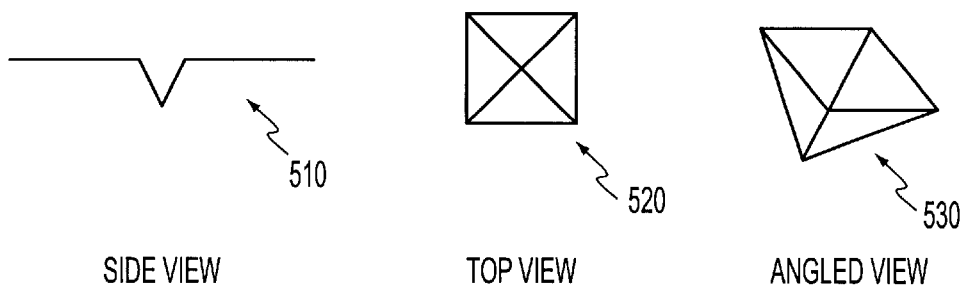
FIG. 5 illustrates an exemplary crystallographic stacking fault defect found on bare silicon wafers.

In a preferred embodiment of the present invention the surface scanning inspection system of FIG. 4 is used to scan bare silicon wafers to detect stacking fault defects which may include crystallographic defects or mounds. FIG. 5 shows a side view 510, top view 520 and angled view 530 of the stacking fault defect. The stacking fault defect usually contains four facets and lie along the crystal planes of the silicon wafer 130. Therefore, all the stacking fault defect are usually positioned in the same direction. The design parameters of several manufactured products require that the number of stacking faults on the surface of the wafer be minimized. Therefore, it is imperative that an accurate detection of the stacking fault defects be detected. Thus, the bare silicon wafers are pre-aligned from the notch on the wafer, at a specified angle that produces the maximum light scatter that can be detected by the collection optics. For the CR82e, the pre-aligned angle is between 34 and 36 degrees. The CR82e machine design setup offsets the wafers by 10 degrees, therefore the wafer is actually rotated between 44 and 46 degrees from the notch of the wafer and relative to the wafer scan path. Specifically, a rotation of the wafer 45 degrees relative to the wafer scan path has been determined to accurately detect the stacking fault defects found on bare silicon wafers.

Although the scanning of the bare silicon wafers have been discussed with the use of the embodiment of FIG. 4 any surface scanning inspection system may be used to scan the bare silicon wafers to detect the mound defects. The same angle of rotation to obtain the maximum light scatter that is collected by the collection optics, also may be the same for any number of surface scanning inspection system.

It should be noted that the wafers 130 may be pre-aligned prior to being inserted into the surface scanning inspection system or the surface scanning inspection system may contain means to pre-align the wafers. A program may also be implemented into the surface scanning inspection system to automatically pre-align the wafers 130 or the pre-align angle may be inserted by the operator of the surface scanning inspection system prior to scanning the wafers 130.

While this invention has been described in conjunction with the exemplary embodiments outlined above, it is evident that many alternatives, modifications and variations will be apparent to those skilled in the art. Accordingly, the exemplary embodiments of the invention may be made without departing from the spirit and scope of the invention.

What is claimed is:

1. A scanning system for use with wafers, comprising:
   a scanner that emits light towards the wafer;
   a scattered light collector that receives scattered light scattered from the wafer; and
   an aligning device that aligns the wafer at a specified orientation prior to the wafer receiving the light emitted from the scanner so as to affect an amount of scattered light receivable by the scattered light collector, wherein the wafer defines a trailing end, a notch and an upper surface that intersects the light emitted from the scanner, the wafer being rotated at least one of 34, 35, 36, 44, 45 and 46 degrees relative to a plane perpendicular to the upper surface of the wafer, such that the notch is spaced from the trailing end of the wafer when the wafer is transported through the scanner by a wafer transporter.

2. The scanning system according to claim 1, further comprising a wafer transporter that transports wafers to and from the scanner.

3. The scanning system according to claim 1, further comprising a deflecting device that deflects the scattered light from the wafer to the scattered light collector.

4. The scanning system according to claim 3, further comprising a reflected light collector that receives reflected light from the wafer, wherein the deflecting device deflects reflected light from the wafer to the reflected light collector.

5. The scanning system according to claim 4, wherein the deflecting device includes a series of mirrors.

6. The scanning system according to claim 1, further comprising a determining device that determines defects of the wafer based on the scattered light collected by the scattered light collector.

7. The scanning system according to claim 6, wherein the defects includes stacking fault defects.

8. The scanning system according to claim 1, wherein the scanner includes a laser that emits a laserbeam towards the wafer.

9. The scanning system according to claim 1, wherein the wafer is a bare silicon wafer and defects to be detected are stacking fault defects located on the bare silicon wafer.

10. The scanning system according to claim 1, wherein the wafer is rotated at least one of 44, 45, and 46 degrees relative to the plane perpendicular to the upper surface of the wafer, such that the notch is spaced from the trailing end of the wafer when the wafer is transported through the scanner by the wafer transporter.

11. The scanning system according to claim 10, wherein the wafer is rotated 45 degrees relative to the plane perpendicular to the upper surface of the wafer.

12. The scanning system according to claim 1, wherein the wafer is rotated at least one of 34, 35, and 36 degrees relative to the plane perpendicular to the upper surface of the wafer, such that the notch is spaced from the trailing end of the wafer when the wafer is transported through the scanner by the wafer transporter.

13. The scanning system according to claim 1, wherein the wafer defines a notch and a center point, and the scanner emits a laser beam towards the wafer along a laser scan path, the wafer being oriented such that a line defined by the notch and the center point of the wafer intersects the laser scan path at a substantially 45 degree angle so as to increase an amount of scattered light received by the scattered light collector.

14. A method of scanning a wafer, comprising the steps of:

emitting light towards the wafer;

receiving scattered light scattered from the wafer; and aligning the wafer at a specified orientation, prior to receiving the emitted light, so as to affect an amount of scattered light receivable by the scattered light collector, wherein the wafer defines a trailing end, a notch and an upper surface that intersects the light emitted from a scanner, the wafer being rotated at least one of 34, 35, 36, 44, 45 and 46 degrees relative to a plane perpendicular to the upper surface of the wafer, such that the notch is spaced from the trailing end of the wafer when the wafer is transported through the scanner by a wafer transporter.

15. The method of claim 14, further comprising a wafer transporter that transports wafers to and from the scanner.

16. The method of claim 14, further comprising a deflecting device that deflects the scattered light from the wafer to the scattered light collector.

17. The method of claim 16, further comprising a reflected light collector that receives reflected light from the wafer, wherein the deflecting device deflects reflected light from the wafer to the reflected light collector.

18. The method of claim 17, wherein the deflecting device includes a series of mirrors.

19. The method of claim 14, further comprising a determining device that determines defects of the wafer based on the scattered light collected by the scattered light collector.

20. The method of claim 19, wherein the defects includes stacking fault defects.

21. The method of claim 14, wherein the scanner includes a laser that emits a laser beam towards the wafer.

22. The method of claim 14, wherein the wafer is a bare silicon wafer and defects to be located are stacking fault defects detected on the bare silicon wafer.

23. The method of claim 14, wherein the wafer is rotated at least one of 44, 45, and 46 degrees relative to the plane perpendicular to the upper surface of the wafer, such that the notch is spaced from the trailing end of the wafer when the wafer is transported through the scanner by the wafer transporter.

24. The method of claim 23, wherein the pre-aligned angle is 45 degrees.

25. The method of claim 14, wherein the wafer is rotated at least one of 34, 35, and 36 degrees relative to the plane perpendicular to the upper surface of the wafer, such that the notch is spaced from the trailing end of the wafer when the wafer is transported through the scanner by the wafer transporter.

26. The method of claim 14, wherein the wafer defines a notch and a center point, the emitting step includes emitting a laser beam towards the wafer along a laser scan path, and the aligning step includes aligning the wafer such that a line defined by the notch and the center point of the wafer intersects the laser scan path at a substantially 45 degree angle so as to increase an amount of scattered light received by the scattered light collector.

27. A scanning system for use with wafers, comprising:

means for emitting light towards the wafer;

means for receiving scattered light scattered from the wafer; and means for aligning the wafer at a specified orientation, prior to receiving the emitted light, so as to affect an amount of scattered light receivable by the means for receiving, wherein the wafer defines a trailing end, a notch and an upper surface that intersects the light emitted from a scanner, the wafer being rotated at least one of 34, 35, 36, 44, 45 and 46 degrees relative to a plane perpendicular to the upper surface of the wafer, such that the notch is spaced from the trailing end of the wafer when the wafer is transported through the scanner by a wafer transporter.

* * * * *